United States Patent [19]

Payne et al.

[11] Patent Number: 4,966,765
[45] Date of Patent: Oct. 30, 1990

[54] **NOVEL COLEOPTERAN-ACTIVE *BACILLUS THURINGIENSIS* ISOLATE**

[75] Inventors: Jewel Payne; Michelle Burrascano; George G. Soares, all of San Diego, Calif.

[73] Assignee: Mycogen Corporation, San Diego, Calif.

[21] Appl. No.: 159,144

[22] Filed: Feb. 23, 1988

[51] Int. Cl.$^5$ .................. C12N 1/20; A61K 39/07; A01N 63/00; A01N 25/12
[52] U.S. Cl. .................. 424/93; 435/252.5; 435/252.1; 435/832; 530/350; 530/825
[58] Field of Search .......... 424/93; 405/832, 252.5, 405/252.1; 530/350, 825

[56] References Cited

U.S. PATENT DOCUMENTS

| | | | |
|---|---|---|---|
| 3,150,062 | 9/1964 | Greenberg et al. | 424/93 |
| 3,946,107 | 3/1976 | Westall | 424/93 |
| 4,467,036 | 8/1984 | Schnepf et al. | 424/93 X |
| 4,695,455 | 9/1987 | Barnes et al. | 424/93 |
| 4,764,372 | 8/1988 | Herrnstadt et al. | 424/93 |
| 4,766,203 | 8/1988 | Krieg et al. | 530/370 |
| 4,771,131 | 9/1988 | Herrnstadt et al. | 424/93 |
| 4,797,276 | 1/1989 | Herrnstadt et al. | 424/93 |
| 4,849,217 | 7/1989 | Soares et al. | 424/93 |
| 4,853,331 | 8/1989 | Herrnstadt | 435/252.1 |

FOREIGN PATENT DOCUMENTS 0202739 11/1986 European Pat. Off.

OTHER PUBLICATIONS

Biol. Abst. 77 (1984), 58279, Cantwell et al.
Biol. Abst. 79 (1985), 20689, Cantwell et al.
Chem. Abst. 89 (1978), 158714h, Galani et al.
Couch, T. L. (1980) "Mosquito Pathogenicity of *Bacillus thuringiensis* var. *israelensis*," Developments in Industrial Microbiology 22:61–76.
Beegle, C. C. (1978) "Use of Entomogenous Bacteria in Agroecosystems," Developments in Industrial Microbiology 20:97–104.
Krieg, A., Huger, A. M., Langenbruch, G. A., and Schnetter, W. (1983) "A New Pathotype Effective Against Coleoptera Larvae," Z. ang. Ent. 96:500–508.

*Primary Examiner*—Howard E. Schain
*Attorney, Agent, or Firm*—Saliwanchik & Saliwanchik

[57] ABSTRACT

The subject invention concerns a novel and useful insecticide with activity against insect pests of the order Coleoptera. Pests in the order Coleoptera do heavy damage to crops, e.g., corn. The insecticide of the subject invention is a novel *B. thuringiensis* microbe referred to as B.t. PS86B1, or mutants thereof. The spores or crystals of this microbe are useful to control coleopteran pests in various environments.

12 Claims, 2 Drawing Sheets

a. <u>B.t.sd.</u> UNDIGESTED
b. <u>B.t.sd.</u> DIGESTED WITH <u>EcoRI</u>
c. <u>B.t.</u> PS86BI UNDIGESTED
d. <u>B.t.</u> PS86BI DIGESTED WITH <u>EcoRI</u>
e. λ-<u>Hind</u> III MARKERS

NOVEL COLEOPTERAN-ACTIVE *BACILLUS THURINGIENSIS* ISOLATE

BACKGROUND OF THE INVENTION

*Bacillus thuringiensis* (B.t.) produces an insect toxin designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of B.t. covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. israelensis," Developments in Industrial Microbiology 22:61-76; Beegle, C.C., (1978) "Use of Entomogenous Bacteria in Agroecosystems," Developments in Industrial Microbiology 20:97-104. Krieg, et al., Z. ang. Ent. (1983) 96:500-508, describe a B.t. isolate named *Bacillus thuringiensis* var. tenebrionis, which is reportedly active against two beetles in the order Coleoptera. These are the Colorado potato beetle, *Leptinotarsa decemlineata*, and *Agelastica alni*.

In European Patent Application No. 0 202 739 there is disclosed a novel B.t. isolate active against Coleoptera. It is known as *B. thuringiensis* var. san diego (B.t.sd.).

Coleopteran-active strains, such as B.t.sd., can be used to control foliar-feeding beetles. The Colorado potato beetle (*Leptinotarsa decemlineata*), for example, is susceptible to the delta-endotoxin of B.t.sd. and larvae are killed upon ingesting a sufficient dose of spore/crystal preparation on treated foliage.

A number of crops are attacked by flea beetles. These beetles belong to the family Chrysomelidae, the decemlineata. The adults can cause extensive damage by feeding on the foliage.

BRIEF SUMMARY OF THE INVENTION

The subject invention concerns a novel *Bacillus thuringiensis* (B.t.) isolate which has activity against coleopteran pests., For example, the novel B.t. isolate, known herein as *Bacillus thuringiensis* PS86B1 (B.t. PS86B1), has thus far been shown to be active against the Colorado potato beetle (*Leptinotarsa decemlineata*). More extensive host range studies are in progress.

The subject invention also includes mutants of B.t. PS86B1 which have substantially the same pesticidal properties as B.t. PS86B1. Procedures for making mutants are well known in the microbiological art. Ultraviolet light and nitrosoguanidine are used extensively toward this end.

Further, the invention also includes the treatment of substantially intact B.t. PS86B1 cells to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated B.t. PS86B1 cell acts as a protective coating for the pesticidal toxin. The toxin becomes available to act as such upon ingestion by a target insect.

DETAILED DISCLOSURE OF THE INVENTION

The novel *Bacillus thuringiensis* isolate of the subject invention has the following characteristics

Characteristics of B.t. PS86B1

Colony morphology—Large colony, dull surface, typical B.t.
Vegetative cell morphology—typical B.t.
Culture methods—typical for B.t.
Flagellar serotyping—PS86B1 belongs to serovar 9, tolworthi.
Inclusions—a non-refractile, flat, pointed ellipse, plus several very small inclusions.
Plasmid preparations—agarose gel electrophoresis of plasmid preparations distinguishes B.t. PS86B1 from B.t.sd. and other B.t. isolates.
Alkali-soluble proteins—SDS polyacrylamide gels show 61,000, 68,000, and 75,000 dalton proteins.
Coleopteran toxin—Bioassay shows activity against Colorado potato beetle with an $LC_{50}$ of 8.4 μg/ml.

A comparison of the characteristics of the well-known B.t. strains *B. thuringiensis* var. kurstaki (HD—1), *B. thuringiensis* var. san diego (B.t.sd.) and *B. thuringiensis* PS86B1 (B.t. PS86B1) is shown in Table 1.

TABLE 1

| Comparison of B.t. HD-1, B.t. PS86B1, and B.t.sd. | | | |
|---|---|---|---|
| | B.t. HD-1 | B.t. PS86B1 | B.t.sd. |
| Serovar | kurstaki | tolworthi | morrisoni |
| Type of inclusion | Bipyramid | flat, pointed ellipse, plus sm. inclusions | square wafer |
| Size of alkali-soluble proteins | 130,000 60,000 | 75,000 68,000 61,000 | 64,000 |
| Host range | Lepidoptera | Coleoptera | Coleoptera |

BRIEF DESCRIPTION OF THE DRAWINGS

FIG. 1: A Photograph of a Standard SDS Polyacrylamide Gel of B.t.sd. and B.t. PS86B1

Figure 2:
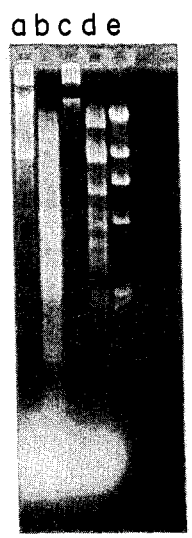
FIG. 2: A Phototograph of Plasmid Preparations from B.t.sd. and B.t. PS86B1

The culture disclosed in this application has been deposited in the Agricultural Research Service Patent Culture Collection (NRRL), Northern Regional Research Center, 1815 North University Street, Peoria, Ill. 61604, USA.

| Culture | Repository No. | Deposit date |
|---|---|---|
| *Bacillus thuringiensis* PS86B1 | NRRL B-18299 | Feb. 3, 1988 |

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

B.t. PS86B1, NRRL B-18299, can be cultured using standard art media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

Formulated products can be sprayed or applied onto foliage to control phytophagous beetles or caterpillars.

Another approach that can be taken is to incorporate the spores and crystals of B.t. PS86B1 into bait granules containing an attractant and applying these granules to the soil for control of soil-inhabiting Coleoptera. Formulated B.t. PS86B1 can also be applied as a seed-coating or root treatment or total plant treatment.

The B.t. PS86B1 cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., Animal Tissue Techniques, W.H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Following are examples which illustrate procedures, including the best mode, for practicing the invention. These examples should not be construed as limiting. All percentages are by weight and all solvent mixture proportions are by volume unless otherwise noted.

EXAMPLE 1—CULTURING B.t. PS86B1, NRRL B-18299

A subculture of B.t. PS86B1, NRRL B-18299 can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2—Testing of B.t. PS86B1, NRRL B-18299 Spores and Crystals

B.t. PS86B1, NRRL B-18299 spores and crystals were tested against the Colorado potato beetle (CPB). B.t. PS86B1 has an $LC_{50}$ of 8.4 μg protein/ml in the CPB assay. The assay for the Colorado potato beetle was conducted as follows:

CPB Bioassay—Early second instar larvae of *Leptinotarsa decemlineata* are placed on potato leaves which have been dipped in suspensions containing *Bacillus thuringiensis* preparations. The larvae are incubated at 25° C. for 4 days, and larval mortality is recorded and analyzed using probit analysis.

We claim:

1. A process for controlling coleopteran insect pests which comprises contacting said insect pests with an insect-controlling effective amount of *B. thuringiensis* PS86B1 having the identifying characteristics of NRRL B-18299, or mutants thereof.

2. A process, according to claim 1, wherein said insect pest is contacted with an insect-controlling sufficient amount of *B. thuringiensis* PS86B1, by incorporating said *B. thuringiensis* PS86B1 into a bait granule and placing said granule on or in the soil when planting seed of a plant upon which plant insect pest is known to feed.

3. A process for controlling soil-inhabiting insect pests of the order Coleoptera which comprises
   (1) preparing a bait granule comprising *B. thuringiensis* PS86B1, or mutants thereof, spores or crystals; and
   (2) placing said bait granule on or in the soil.

4. A process, according to claim 3, wherein said bait granule is applied at the same time corn seed is planted in the soil.

5. A process, according to claims 1 or 4, wherein substantially intact B.t. PS86B1 cells, or mutants thereof, are treated to prolong the pesticidal activity when the substantially intact cells are applied to the environment of a target pest.

6. A composition of matter comprising *B. thuringiensis* PS86B1, or mutants thereof, spores or crystals in association with an insecticide carrier.

7. A composition of matter, according to claim 6, wherein said carrier comprises beetle phagostimulants or attractants.

8. A composition of matter comprising *B. thuringiensis* PS86B1, or mutants thereof, in association with formulation ingredients applied as a seed coating.

9. A biologically pure culture of *Bacillus thuringiensis* PS86B1, having the identifying characteristics of NRRL B-18299, or mutants thereof, having activity against insect pests of the order Coleoptera.

10. A process, according to claim 1, wherein the coleopteran pests are present on stored products.

11. A process, according to claim 1, wherein the coleopteran pest is the Colorado potato beetle.

12. A toxin(s) active against coleopteran pests, said toxin(s) produced by a biologically pure culture of *B. thuringiensis* PS86B1, having the identifying characteristics of NRRL B-18299.

* * * * *

UNITED STATES PATENT AND TRADEMARK OFFICE
CERTIFICATE OF CORRECTION

PATENT NO. : 4,966,765

DATED : October 30, 1990

INVENTOR(S) : Jewel Payne, Michelle Burrascano, George G. Soares

It is certified that error appears in the above-identified patent and that said Letters Patent is hereby corrected as shown below:

Column 1: line 25: "tenebrionis" should read --*tenebrionis*--; lines 41-42: "decemlineata" should read --*decemlineata*--; line 57: "nitrcsoguanidine" should read --nitrosoguanidine--.

Column 5: line 1: "claims 1 or 4" should read --claims 1 or 3--.

Column 6: line 3: "formulaticn" should read --formulation--; line 10: "claim 1" should read --claim 2--.

Signed and Sealed this

Third Day of March, 1992

Attest:

HARRY F. MANBECK, JR.

Attesting Officer

Commissioner of Patents and Trademarks